United States Patent [19]

Bailey

[11] Patent Number: 4,478,224
[45] Date of Patent: Oct. 23, 1984

[54] ARTIFACT DETECTOR FOR HEARTBEAT RATE MEASURING SYSTEM

[75] Inventor: Wilber H. Bailey, Leucadia, Calif.

[73] Assignee: Camino Laboratories, Inc., San Diego, Calif.

[21] Appl. No.: 444,782

[22] Filed: Nov. 26, 1982

[51] Int. Cl.³ .............................................. A61B 5/04
[52] U.S. Cl. .................................... 128/706; 128/708; 128/901
[58] Field of Search .............................. 128/695–696, 128/702–704, 706, 708, 901

[56] References Cited

U.S. PATENT DOCUMENTS

| | | | |
|---|---|---|---|
| 3,654,916 | 4/1972 | Neilson | 128/702 |
| 3,791,378 | 2/1974 | Hochberg et al. | 128/901 |
| 3,905,364 | 9/1975 | Cudahy et al. | 128/696 |
| 3,998,214 | 12/1976 | Garrison | 128/702 |
| 4,259,966 | 4/1981 | Cannon et al. | 128/706 |
| 4,301,405 | 11/1981 | Carlson | 128/696 |

Primary Examiner—William E. Kamm
Assistant Examiner—Mitchell J. Shein
Attorney, Agent, or Firm—Fulwider Patton Rieber Lee & Utecht

[57] ABSTRACT

A heartbeat rate measuring system for monitoring a patient's EKG signal and estimating heartbeat rate. The system includes an artifact detection apparatus for filtering the EKG signal to detect the occurrence of a heartbeat artifact, and for inhibiting the measuring heartbeat intervals whenever an artifact is detected. The system therefore estimates heartbeat rate based solely on measurements of time intervals between actual heartbeats.

11 Claims, 3 Drawing Figures

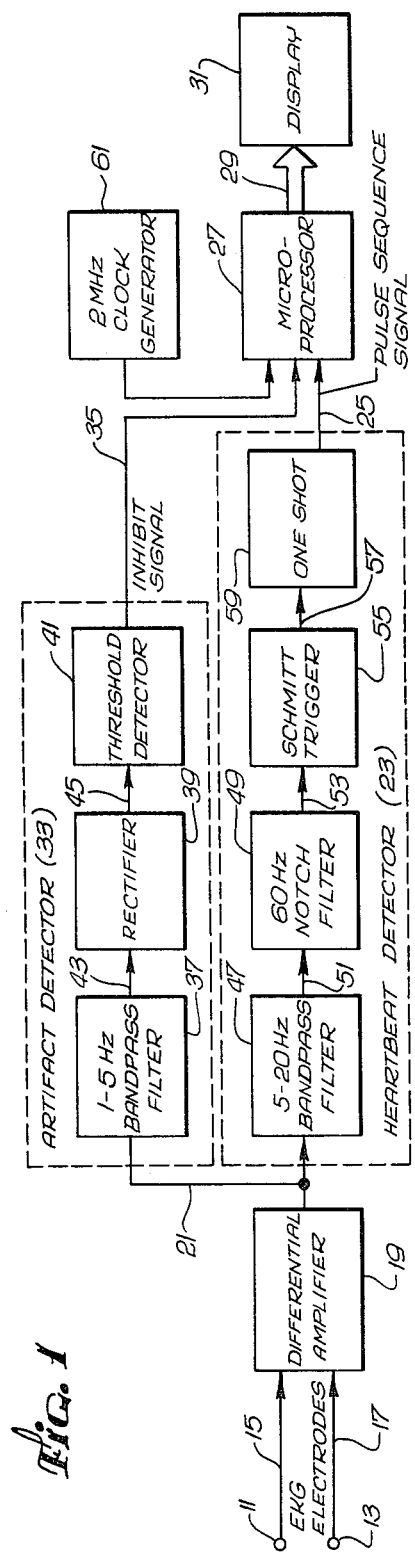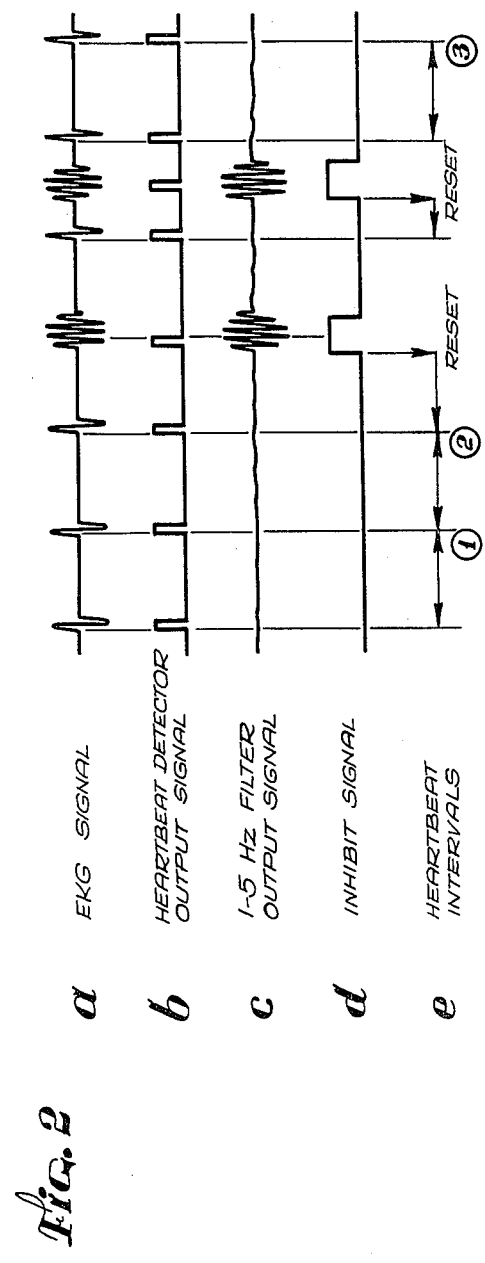

HEART RATE SUBROUTINE

ARTIFACT DETECTOR FOR HEARTBEAT RATE MEASURING SYSTEM

BACKGROUND OF THE INVENTION

This invention relates generally to systems for monitoring an EKG signal and estimating heartbeat rate, and, more particularly, to systems of this kind having means for reducing or eliminating the effects of heartbeat artifacts.

Heartbeat artifacts in an EKG signal can be caused by many factors, including poor continuity between electrodes attached to a patient and movement of the electrode leads. Systems having one electrode located in the patient's mouth are particularly susceptible to artifacts caused by movement of the mouth electrode. This is because use of mouth electrode creates a small battery potential between the electrodes, with any movement of the mouth electrode modulating this potential and thereby creating heartbeat artifacts.

Filtering the EKG signal to remove any heartbeat artifacts is not completely effective, because the artifacts and the actual heartbeart pulses have overlapping frequency spectra. Thus, filtering out the artifacts also filters out a substantial portion of the actual heartbeat pulses.

One technique for reducing the effects of heartbeat artifacts is described in a copending and commonly-assigned application for U.S. Pat. Ser. No. 410,043, filed in the name of Richard L. Foreman and entitled "Continuity Detector For Heartbeat Rate Measuring System." In the disclosed system, a pair of electrodes contact a patient to produce an EKG signal, and heartbeat detection means monitors the signal to detect the successive heartbeat pulses. A microprocessor measures the time intervals between the successive pulses, and estimates heartbeat rate based on those measurements. In addition, a special continuity circuit detects electrical continuity between the two electrodes and inhibits the microprocessor from measuring heartbeat intervals whenever poor continuity is detected. Although this system is generally effective in reducing the effects of heartbeat artifacts caused by poor electrical continuity, it is not believed effective in eliminating the effects of artifacts caused by factors other than poor continuity, such as by movement of the electrodes and electrode leads.

It should therefore be appreciated that there is a need for a heart rate monitoring system that further reduces the effects of heartbeat artifacts in an EKG signal. The present invention fulfills this need.

SUMMARY OF THE INVENTION

The present invention is embodied in a method and appartus for monitoring an EKG signal and estimating heartbeat rate. The apparatus includes first and second electrodes adapted for attachment to a patient at spaced locations, to carry the EKG signal, along with heart rate means for monitoring the EKG signal and estimating heartbeat rate. In accordance with the invention, the apparatus further includes artifact detection means for monitoring the EKG signal to detect heartbeat artifacts and for producing a corresponding inhibit signal, along with means inhibiting the heart rate means whenever the inhibit signal indicates the occurrence of an artifact. Thereafter, if the inhibit signal terminates, the heart rate means is again enabled. In this way, the undesired effects that heartbeat artifacts would otherwise have on the system's estimate of heartbeat rate are eliminated.

When one of the two electrodes is adapted for placement in the patient's mouth, the likelihood of heartbeat artifacts caused by movement of the mouth electrode is particularly high. These artifacts have a frequency spectrum that overlaps the frequency spectrum of the actual heartbeats. Typically, the spectrum of a heartbeat artifact extends between 1 and 10 Hz and the spectrum of an actual heartbeat extends between 5 and 20 Hz. The artifact detection means preferably includes means for filtering the EKG signal to pass only the portion of the artifact's spectrum not common to the actual heartbeat's spectrum, along with means for producing the inhibit signal whenever the amplitude of the filtered EKG signal exceeds a prescribed threshold.

In the preferred embodiment, the heart rate means measures the time intervals between successive heartbeats and estimates heartbeat rate based on a plurality of such time interval measurements. If the inhibit signal ever occurs, indicating the occurrence of a heartbeat artifact, the inhibit means inhibits the heart rate means from continuing to measure the current heartbeat interval. Thereafter, when the inhibit signal terminates, indicating that the artifact is no longer present, the inhibit means permits the heart rate means to resume measuring time intervals after the occurrence of the next heartbeat.

Other aspects and advantages of the invention should become apparent from the following description of the preferred embodiment, taken in conjunction with the accompanying drawings, which illustrate, by way of example, the principles of the invention.

BRIEF DESCRIPTION OF THE DRAWINGS

FIG. 1 is a simplified block diagram of a heart rate monitoring system having an artifact detector embodying the principles of the present invention;

FIG. 2 is a timing diagram showing the waveforms at several different locations in the block diagram of FIG. 1.

DESCRIPTION OF THE PREFERRED EMBODIMENT

Figure 3:
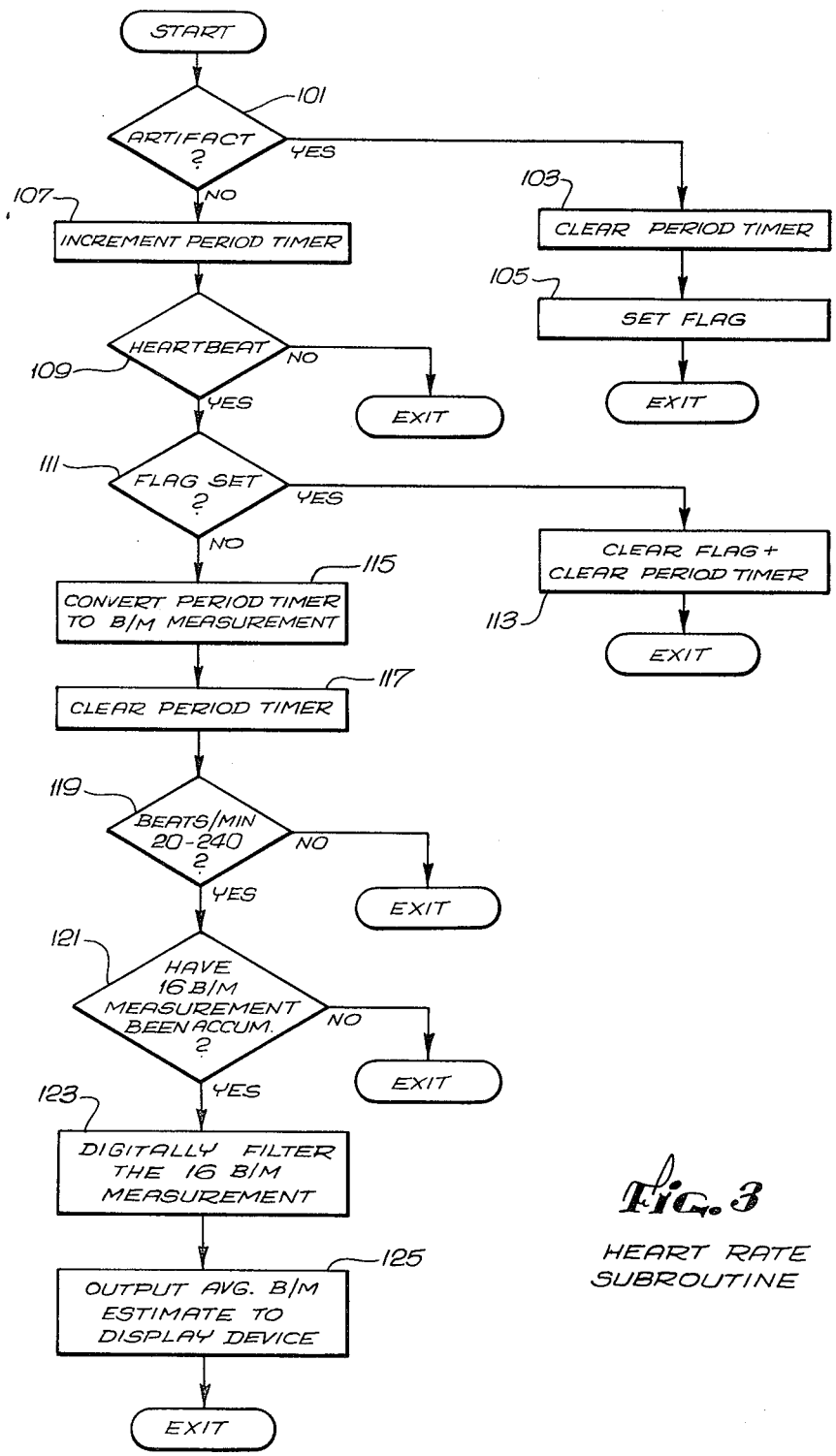
FIG. 3 is a flowchart showing, in simplified form, the operational steps performed by the microprocessor of FIG. 1.

Referring now to the drawings, and particularly to FIG. 1, there is shown an apparatus for monitoring a person's EKG signal and producing an accurate estimate of heartbeat rate. The apparatus includes first and second electrodes 11 and 13 for contacting the person in spaced relationship to each other, to develop an EKG signal indicative of heartbeat activity. In some situations, one of the two electrodes is adapted for placement in the patient's mouth, such that a small battery potential is created between the electrodes. Unfortunately, movement of the mouth electrode modulates this potential, to produce an ac signal that sometimes can have the appearance of a heartbeat, and thus be designated a heartbeat artifact.

The two electrodes 11 and 13 are connected by leads 15 and 17, respectively, to a differential amplifier 19, for detection and amplification of the EKG signal. The amplified EKG signal is coupled as a single-ended signal over line 21 to a heartbeat detector 23, which filters it to detect its successive heartbeats and outputs a corresponding binary pulse sequence signal for coupling on line 25 to a microprocessor 27. An exemplary EKG signal and the corresponding pulse sequence signal are depicted in FIG. 2, lines (a) and (b), respectively.

The microprocessor 27 measures the time intervals between the successive pulses of the pulse sequence siganl supplied on line 25 and converts each measurement to a corresponding rate measurement, expressed in beats per minute. After accumulating a set of 16 such rate measurements, the microprocessor digitally filters the set to produce an estimate of average heartbeat rate. A signal representing this estimate is coupled on lines 29 to a display device 31.

Heartbeat artifacts in the EKG signal will result in additional pulses being included in the pulse sequence signal supplied to the microprocessor 27. The digital filtering effected by the microprocessor can reduce the effects these additional pulses will have on its estimate of heartbeat rate, but ordinarily cannot completely eliminate those effects.

Actual heartbeats in the EKG signal typically have a frequency spectrum in the range of 5 to 20 Hz, whereas heartbeat artifacts in the signal typically have a frequency spectrum in the range of 1 to 10 Hz. Because of the overlap in their respective frequency spectra, it is not generally possible to completely filter out the artifacts without simultaneously filtering out a substantial portion of the actual heartbeat pulses.

In accordance with the invention, the apparatus further includes an artifact detector 33 for monitoring the EKG signal output by the differential amplifier 19 to detect the occurrence of heartbeat artifacts and for producing an inhibit signal for coupling on line 35 to the microprocessor 27, instructing it to temporarily inhibit its measuring of the current heartbeat interval. The microprocessor resumes its measuring of heartbeat intervals if the artifact detector later determines that the artifact is no longer present. In this way, the undesired effects that heartbeat artifacts have on the apparatus' estimate of heartbeat rate are eliminated.

More particularly, the artifact detector 33 includes a 1 to 5 Hz bandpass filter 37, a rectifier 39, and a threshold detector 41. The amplified EKG signal is input to the bandpass filter on line 21 from the differential amplifier 19, to remove substantially all of the actual heartbeat pulses present in it, as shown in FIG. 2, line (c). The filtered signal, which includes primarily heartbeat artifact signal components only is coupled on line 43 to the rectifier for rectification and in turn over line 45 to the threshold detector. The threshold detector compares the rectified signal to a prescribed threshold, to generate the inhibit signal whenever the threshold is exceeded, as shown in FIG. 2, line (d).

The heartbeat detector 23 includes a low-frequency bandpass filter 47 and a 60 Hz notch filter 49, for removing background noise from the single-ended EKG signal output by the differential amplifier 19. The single-ended EKG signal is coupled over line 21 from the differential amplifier to the bandpass filter, which limits the signal to a bandwidth between about 5 and 20 Hz. This bandlimited signal is, in turn, coupled over line 51 to the 60 Hz notch filter, which removes any 60 Hz noise that might have been picked up by the electrodes 11 and 13 and electrode leads 15 and 17.

The filtered EKG signal output by the notch filter 49 includes a number of consecutive pulses caused by actual heartbeats, and additionally might include a number of heartbeat artifacts caused by any of a number of sources, such as movement of the mouth electrode. The filtered EKG signal is coupled over line 53 from the notch filter to a Schmitt trigger 55, and in turn over line 57 to a monostable multi-vibrator or one-shot 59. These latter two devices convert the filtered EKG signal into the pulse sequence signal, as shown in FIG. 2, line (b). The duration of each pulse is preferably on the order of 240 milliseconds. This pulse sequence signal is input on line 25 to the microprocessor 27.

The preferred microprocessor 27 is an NEC 80C49 device. Associated with the microprocessor are a 2 MHz clock generator 61 for appropriately sequencing it through its operations, and the display device 31 for displaying the estimate of heartbeat rate. It will be understood by those of ordinary skill in the art that many other microprocessors, computers, or even hardware circuits might alternatively be used in implementing the invention.

As previously mentioned, the microprocessor 27 measures the time intervals between the successive heartbeats detected by the heartbeat detector 23. Referring to the exemplary pulse sequence signal of FIG. 2, line (b) and the schematic diagram of FIG. 2, line (e), it will be observed that the microprocessor has been able to complete its measuring of the time intervals between the first and second detected pulses and between the second and third detected pulses. While measuring the interval between the third and fourth pulses, however, the inhibit signal (FIG. 2(d)) is input to it by the artifact detector 33, indicating that an artifact is present in the EKG signal and that the measurement of the current heartbeat interval should be terminated. The microprocessor inhibits further measuring of any pulse intervals for as long as the inhibit signal remains present. After the signal terminates, the microprocessor waits for the next heartbeat pulse to arrive before again enabling its measurement of the next time interval. Thus, in the example of FIG. 2, the microprocessor is able to measure the third heartbeat interval only after receipt of the seventh and eighth pulses in the pulse sequence signal.

As each interval measurement is completed, the microprocessor 27 converts it to a corresponding rate measurement, expressed in beats per minute. After the microprocessor has accumulated a set of 16 rate masurements, it digitally filters the set to further reduce the effects of any heartbeat artifacts that might have avoided detection by the artifact detector 33. One suitable filtering algorithm is described in a copending and commonly-assigned application for U.S. Pat. Ser. No. 306,329, filed in the name of Wilber H. Bailey and entitled "Method And Apparatus For Measuring Heartbeat Rate."

Referring now to FIG. 3, there is shown a flowchart of a heart rate subroutine implemented by the microprocessor 27 of FIG. 1. The subroutine is entered at regular intervals separated by approximately two milliseconds. Upon initiation of the apparatus, the microprocessor performs a first step 101 of monitoring the inhibit signal supplied on line 35, to determine whether or not an artifact has been detected during the previous two milliseconds. If one has been detected, the microprocessor clears a period timer being used to time the current heartbeat interval, at step 103, and then sets a "wait" flag, at step 105. It then exits this heart rate subroutine, returning to it approximately two milliseconds after it last entered it.

With reference again to step 101, if it is determined that an artifact has not occurred during the previous two milliseconds, the microprocessor 27 increments the period timer at step 107. The timer is incremented in steps of about two milliseconds, which corresponds to how often the microprocessor implements the heart rate subroutine. In step 109, the microprocessor then monitors the pulse sequence signal on line 25, to determine whether or not a heartbeat has occurred during the previous two milliseconds. If one has not occurred, the microprocessor exits the heart rate subroutine. If a heartbeat has occurred on the other hand, the microprocessor at step 111 determines whether or not the "wait" flag is presently set. If so, it is determined that the heartbeat just detected is the first one following termination of an artifact. The microprocessor then clears both the "wait" flag and the period timer, at step 113, and exits the subroutine. On the other hand, if it is determined at step 111 that the "wait" flag is not set, the microprocessor, at step 115, converts the time measurement currently stored in the period timer to a corresponding rate measurement, expressed in beats per minute, and, at step 117, clears the period timer, putting it in condition to measure the next heartbeat interval.

The microprocessor 27 then determines, at step 119, whether or not the rate measurement just computed is between 20 and 240 beats per minute. If it is not, it is assumed that the measurement is invalid, and the heart rate subroutine is exited. On the other hand, if it is determined that the rate measurement just computed is between 20 and 240 beats per minute, the program proceeds to step 121, where it is determined whether or not 16 rate measurements have been accumulated. If they have not, the heart rate subroutine is exited, to be returned to approximately two milliseconds after it was last entered. On the other hand, if 16 rate measurements have been accumulated, the microprocessor digitally filters this set of measurements, at step 123, and outputs an estimate of heartbeat rate on lines 29 for display by the display device 31, at step 125.

It should be appreciated from the foregoing description that the present invention provides an improved apparatus and method for monitoring a patient's EKG signal and reliably estimating heartbeat rate. The apparatus continuously monitors the EKG signal to detect the occurrence of heartbeat artifacts and inhibits its measuring of the current heartbeat interval whenever an artifact is detected. This eliminates the effects any heartbeat artifacts might have on the apparatus' estimate of heartbeat rate.

Although the present invention has been described in detail with reference to the presently preferred embodiment, it should be understood by those of ordinary skill in the art that various modifications can be made without departing from the invention. Accordingly, the invention is limited only by the following claims.

I claim:

1. Apparatus for monitoring an EKG signal and estimating heartbeat rate, comprising:
    first and second electrodes adapted to contact a patient and transmit an EKG signal indicative of heartbeat activity;
    heart rate means, connected to the first and second electrodes, for monitoring the EKG signal and estimating heartbeat rate;
    artifact detection means for monitoring the EKG signal to detect the occurrence of heartbeat artifacts therein and for producing a corresponding inhibit signal; and
    means for inhibiting the heart rate means in response to the inhibit signal, whereby the estimate of heartbeat rate is substantially unaffected by the occurrence of heartbeat artifacts.

2. Apparatus as defined in claim 1, wherein:
    the frequency spectrum of any heartbeat artifacts present in the EKG signal overlaps the frequency spectrum of the actual heartbeats; and
    the artifact detection means includes
        means for filtering the EKG signal to pass only the portion of the frequency spectrum of the heartbeat artifacts not common to the frequency spectrum of the actual heartbeats, and
        means for producing the inhibit signal whenever the amplitude of the filtered EKG signal exceeds a prescribed threshold.

3. Apparatus as defined in claim 2, wherein the means for filtering has a bandwidth of about one Hz to about five Hz.

4. Apparatus as defined in claim 1, wherein:
    the heart rate means includes
        means for measuring the time intervals between successive heartbeats, and
        means for estimating heartbeat rate based on a plurality of such time interval measurements; and
    the means for inhibiting inhibits the means for measuring if the inhibit signal occurs at any time between successive heartbeats.

5. Apparatus as defined in claim 1, wherein one of the first and second electrodes is adapted to be placed in the mouth of the patient.

6. Apparatus for monitoring an EKG signal and estimating heartbeat rate, comprising:
    first and second electrodes adapted to contact a patient and transmit an EKG signal indicative of heartbeat activity, one of the electrodes being adapted to be placed in the mouth of the patient;
    heart rate means, connected to the first and second electrodes, for measuring the time intervals between successive heartbeats present in the EKG signal and estimating heartbeat rate based on a plurality of such time interval measurements;
    artifact detection means for monitoring the EKG signal to detect the occurrence of heartbeat artifacts therein and for producing a corresponding inhibit signal;
    wherein the frequency spectrum of any heartbeat artifacts present in the EKG signal overlaps the frequency spectrum of the actual heartbeats;
    wherein the artifact detection means includes
        bandpass filter means having a bandwidth of about one Hz to about five Hz, for filtering the EKG signal to pass only the portion of the frequency spectrum of the heartbeat artifacts not common to the frequency spectrum of the actual heartbeats, and
        means for producing the inhibit signal whenever the amplitude of the filtered EKG signal exceeds a prescribed threshold; and
    means for inhibiting the heart rate means from measuring the current heartbeat interval if the inhibit signal occurs at any time between the successive heartbeats, whereby the estimate of heartbeat rate is substantially unaffected by the occurrence of heartbeat artifacts.

7. A method for monitoring an EKG signal and estimating heartbeat rate, comprising steps of:

connecting first and second electrodes to a patient, for transmitting an EKG signal indicative of heartbeat activity;

estimating heartbeat rate based on the EKG signal present on the first and second electrodes;

detecting the occurrence of heartbeat artifacts in the EKG signal and producing a corresponding inhibit signal; and inhibiting the step of estimating in response to the inhibit signal, whereby the estimate of heartbeat rate is substantially unaffected by the occurrence of heartbeat artifacts.

8. A method as defined in claim 7, wherein:

the frequency spectrum of any heartbeat artifacts present in the EKG signal overlaps the frequency spectrum of the actual heartbeats; and the step of detecting includes
steps of filtering the EKG signal to pass only the portion of the frequency spectrum of the heartbeat artifacts not common to the frequency spectrum of the actual heartbeats, and producing the inhibit signal whenever the amplitude of the filtered EKG signal exceeds a prescribed threshold.

9. A method as defined in claim 8, wherein the step of filtering extracts the portion of the frequency spectrum extending between about one Hz to about five Hz.

10. A method as defined in claim 7, wherein:

the step of estimating includes steps of
measuring the time intervals between successive heartbeats, and
estimating heartbeat rate based on a plurality of such time interval measurements; and the step of inhibiting inhibits the step of measuring if the inhibit signal occurs at any time between successive heartbeats.

11. A method as defined in claim 7, wherein the step of connecting places one of the first and second electrodes in the mouth of the patient.

* * * * *